United States Patent
Aoki

(10) Patent No.: US 8,635,912 B2
(45) Date of Patent: Jan. 28, 2014

(54) RECORDING MEDIUM DETERMINATION APPARATUS AND IMAGE FORMING APPARATUS

(75) Inventor: Masaru Aoki, Numazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 523 days.

(21) Appl. No.: 12/967,309

(22) Filed: Dec. 14, 2010

(65) Prior Publication Data

US 2011/0142459 A1 Jun. 16, 2011

(30) Foreign Application Priority Data

Dec. 16, 2009 (JP) .................................. 2009-285756
Oct. 20, 2010 (JP) .................................. 2010-235489

(51) Int. Cl.
*G01N 29/07* (2006.01)
*G03G 15/00* (2006.01)

(52) U.S. Cl.
USPC .................. 73/597; 73/159; 73/602; 399/389

(58) Field of Classification Search
USPC ............................. 73/602, 597, 159; 399/389
See application file for complete search history.

(56) References Cited

U.S. PATENT DOCUMENTS

| 4,446,735 | A | 5/1984 | Weilacher | |
|---|---|---|---|---|
| 5,621,173 | A * | 4/1997 | Knorr | 73/610 |
| 2002/0079141 | A1* | 6/2002 | Luque | 177/1 |
| 2009/0003857 | A1 | 1/2009 | Kuramochi et al. | |
| 2009/0310981 | A1* | 12/2009 | Ishida | 399/17 |
| 2009/0310992 | A1* | 12/2009 | Iwasa et al. | 399/45 |
| 2011/0142461 | A1* | 6/2011 | Nakamura et al. | 399/45 |

FOREIGN PATENT DOCUMENTS

| JP | 1-39540 B | 8/1982 |
|---|---|---|
| JP | 57-132055 A | 8/1982 |
| JP | 9-218225 A | 8/1997 |
| JP | 2004-107030 A | 4/2004 |
| JP | 2009-029622 A | 2/2009 |

* cited by examiner

*Primary Examiner* — Peter Macchiarolo
*Assistant Examiner* — Rose M Miller
(74) *Attorney, Agent, or Firm* — Canon USA Inc. IP Division

(57) ABSTRACT

The timing of obtaining an output value for use in a determination of a recording medium is generated from a received ultrasonic wave and a waveform generated by delaying the ultrasonic wave, whereby it is possible to reduce an influence of a reflection wave from the peripheral members and an influence of a change in the environment to improve the accuracy of determination of the recoding medium.

6 Claims, 11 Drawing Sheets

RECORDING MEDIUM DETERMINATION APPARATUS AND IMAGE FORMING APPARATUS

BACKGROUND OF THE INVENTION

1. Field of the Invention

The present invention relates to a determination apparatus for determining a type of a recording medium and an image forming apparatus equipped with the determination apparatus.

2. Description of the Related Art

In a conventional image forming apparatus, a user sets a type of a recording medium (hereinafter also referred to as "paper type"), for example, by setting at a computer serving as an external apparatus or using an operation panel provided in the main body of the image forming apparatus. By setting a type of a recording medium, image forming conditions can be changed according to a type of a recording medium, and image formation is carried out under the conditions suitable for the type of the recording medium. To reduce the load of such user setting through a computer or an operation panel, recently, an image forming apparatus has been provided with, for example, a sensor capable of determining a type of a recording medium inside the image forming apparatus so that a type of a recording medium is automatically determined.

For example, "Japanese Patent Application Laid-Open No. 57-132055" discusses a method in which, when a grammage of a recording medium is measured with use of an ultrasonic wave, a propagation time of an ultrasonic wave between an ultrasonic transmitter and an ultrasonic receiver is calculated in advance, and the grammage is measured based on the calculated propagation time.

However, the environment where a recording medium determination apparatus is disposed is not always under a constant temperature and atmospheric pressure. Therefore, a variation in the environment brings about a change in the propagation speed of an ultrasonic wave in the air, so that detection based on a propagation time calculated in advance may not produce an accurate measurement result.

SUMMARY OF THE INVENTION

The invention of the present application is directed to quickly obtaining an accurate measurement result even if a recording medium is detected without calculating a propagation time of an ultrasonic wave in advance.

According to an aspect of the present invention, a recording medium determination apparatus includes a transmitting unit configured to transmit an ultrasonic wave to a recording medium; a receiving unit configured to receive the ultrasonic wave which has passed through the recording medium; a delay unit configured to generate a delay signal delayed for a predetermined time relative to the received ultrasonic wave based on the received ultrasonic wave; a generation unit configured to generate a timing of detecting an output value of the received ultrasonic wave from the received ultrasonic wave and the delay signal; and a control unit configured to determine the recording medium using the output value of the received ultrasonic wave at the timing generated by the generator.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Hereinafter, exemplary embodiments of the present invention will be described with reference to the drawings. It should be understood that the following exemplary embodiments do not intend to limit the invention defined by the appended claims, and all the combinations of the features described in the exemplary embodiments are not necessarily essential to the solution according to the invention.

Figure 1:
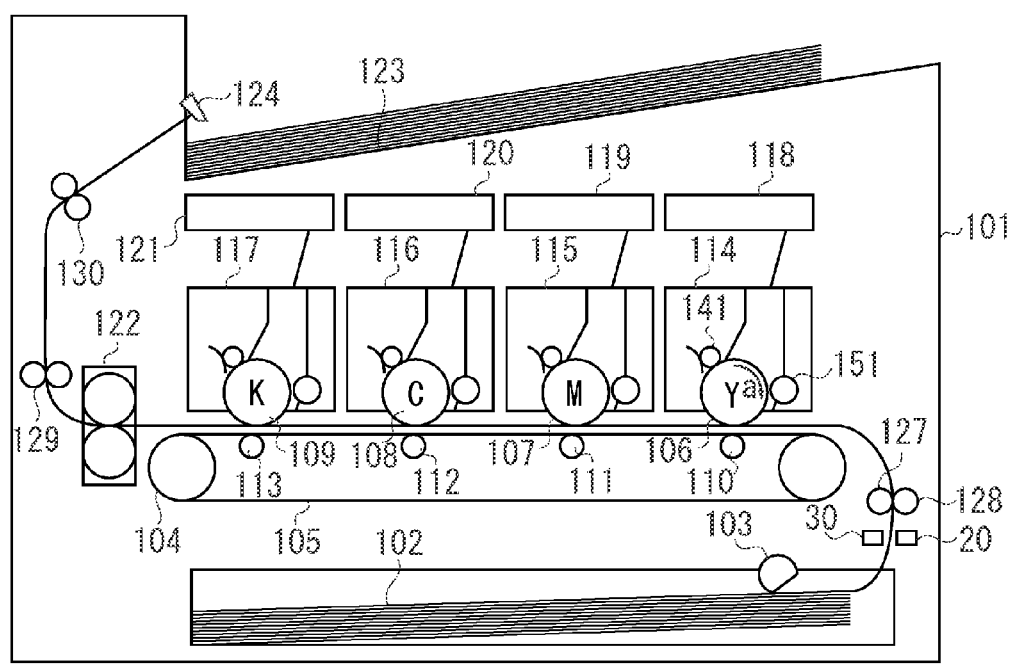
FIG. 1 is a schematic view of an image forming apparatus according to exemplary embodiments of the present invention.

A recording medium determination apparatus according to exemplary embodiments of the present invention, which determines a type of a recording medium, can be used in an image forming apparatus such as a copying machine or a printer. FIG. 1 illustrates an example of a configuration of an image forming apparatus where the recording medium determination apparatus is mounted.

First, the configurations of the respective units of an image forming apparatus will be described. An image forming apparatus 101 forms an image. A recording media P is placed on a sheet forming cassette 102. A sheet feeding roller 103 feeds the recording medium P placed on the sheet feeding cassette 102. An ultrasonic transmitter 20 transmits an ultrasonic wave for a determination of the recording medium P. An ultrasonic receiver 30 receives the ultrasonic wave transmitted from the ultrasonic transmitter 20. The ultrasonic transmitter 20 and the ultrasonic receiver 30 are defined as a recording medium determination apparatus. Conveyance rollers 127 and 128 convey the recording medium P. A transfer belt drive roller 104 drives a transfer belt to rotate. The transfer belt 105 is driven by the transfer belt drive roller 104.

Images are formed on photosensitive drums 106 to 109 by yellow, magenta, cyan, and black toners, respectively. Transfer rollers 110 to 113 respectively correspond to the photosensitive drums 106 to 109 of the respective colors, and transfer images formed on the photosensitive drums 106 to 109, to the recording medium P conveyed on the transfer belt 105. Cartridges 114 to 117 are used to form yellow, magenta, cyan, and black images, respectively. Optical units 118 to 121 form latent images on the photosensitive drums 106 to 109 to create yellow, magenta, cyan, and black images. A fixing unit 122 fixes an image formed on the recording medium P. Paper discharge rollers 129 and 130 discharge the recording medium P on which an image is fixed by the fixing unit 122. The recording medium P is discharged to a discharge tray 123. A full-state detection sensor 124 detects a full-stacked state of the discharge tray 123.

Next, an image forming operation of the image forming apparatus 101 will be described. Print data including, for example, a print instruction and image information is input from, for example, a host computer (not shown) to the image forming apparatus 101. Then, the image forming apparatus 101 starts a print operation, and the recording medium P is sent from the paper feeding cassette 102 onto the conveyance path by the paper feeding roller 103. The photosensitive drums 106, 107, 108, and 109 are charged to have a certain electric potential by charging rollers in the image forming operation. The optical units 118, 119, 120, and 121 form electrostatic latent images by exposure-scanning the surfaces of the charged photosensitive drums 106, 107, 108, and 109 with laser beams according to the input print data to form a latent image. Development apparatuses in the cartridges 114, 115, 116, and 117 carry out developments to visualize the formed electrostatic latent image. The developed images are transferred onto the recording medium P. The images transferred onto the recording medium P is fixed thereon by the fixing unit 122 constituted by, for example, a fixing roller. The recording medium P with the images fixed thereon is discharged to the discharge tray 123 by the paper discharge roller 130, and then the image forming operation is finished.

Figure 2:
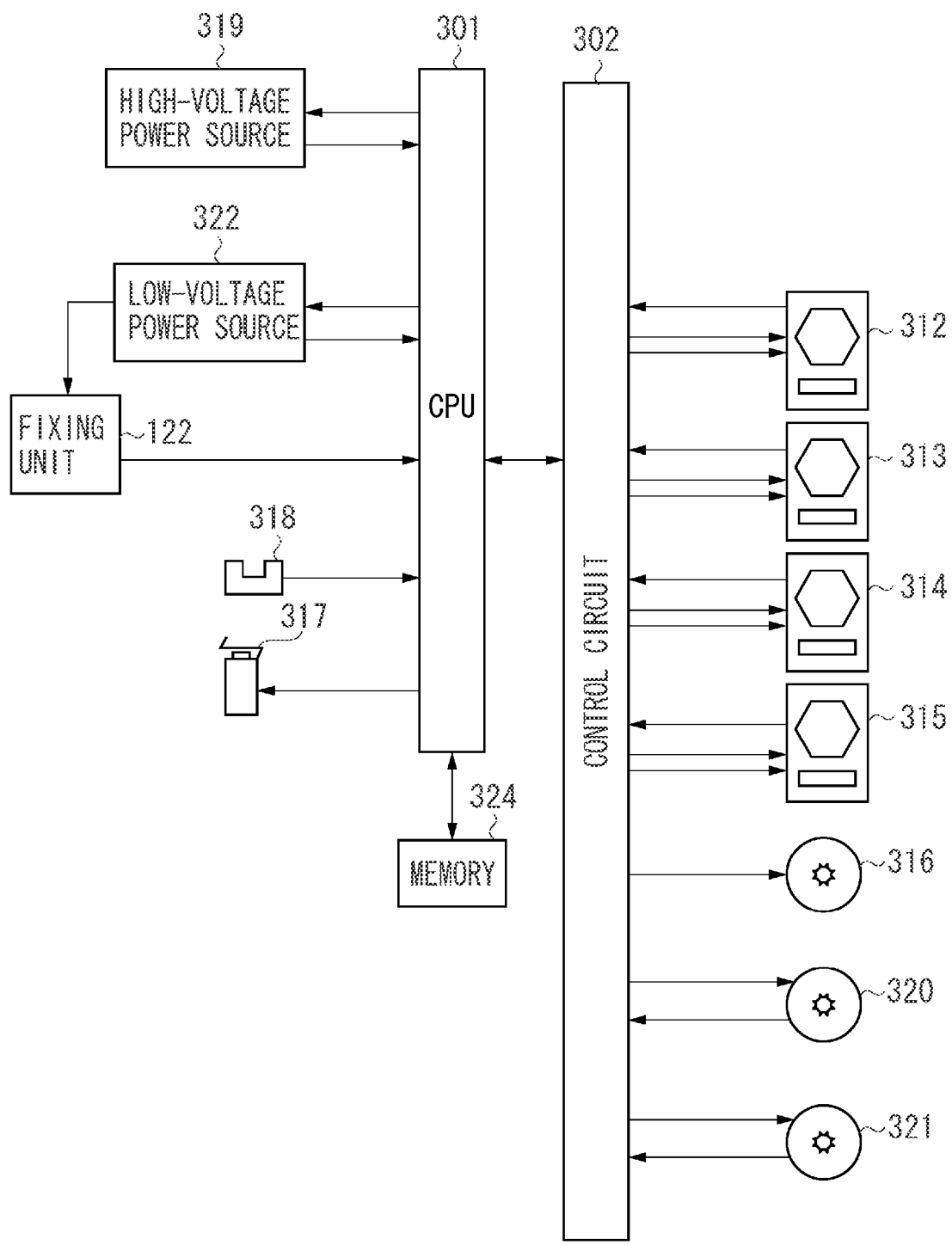
FIG. 2 is a block diagram of a control unit performing an operation control according to the exemplary embodiments of the present invention.

FIG. 2 is an exemplary block diagram of a control unit which controls an operation of the image forming apparatus 101. A central processing unit (CPU) 301 is connected through a control circuit 302 to optical units 312 to 315 for the respective colors which each include, for example, a polygonal mirror, a motor, and a laser emitting element. The CPU 301 controls the optical units 312 to 315 by outputting a control signal to the control circuit 302, to form latent images by scanning the photosensitive drums 106 to 109 with laser. Similarly, the CPU 301 controls, for example, a paper feeding motor 316 for driving the paper feeding roller 103 and the conveyance roller 128 to convey the recording medium P. Further, the CPU 301 perform control to maintain a fixing temperature at a constant temperature by monitoring the temperature with use of a thermistor (not shown) disposed at the fixing unit 122. Further, the CPU 301 is connected to a memory 324 through, for example, a bus (not shown), and controls an operation with use of a program and data stored in the memory 324.

The CPU 301 performs control to change, for example, a fixing condition of the recording medium P according to a determination result of the recording medium determination apparatus. More specifically, a high temperature is set as the fixing temperature for a relatively thick recording medium P since the thick recording medium has a large heat capacity, while a low temperature is set as the fixing temperature for a relatively thin recording medium P since the thin recording medium has a small heat capacity. The CPU 301 can also change the above-mentioned fixing temperature condition based on a detection value itself without determining the recording medium P, which can be realized by having the memory 324 store a table containing detection values and fixing temperature conditions corresponding to the detection values such that they are associated with each other. The control target is not limited to the fixing condition, and the detection value may be fed-back to, for example, the conveyance speed. The control circuit 302 controls the motor speeds within the optical units 312 to 315 and the speed of the paper feeding motor 316 according to an instruction of the CPU 301. A load to the CPU 301 can be reduced by constructing a control means by a hardware circuit, like the control circuit 302.

Figure 3:
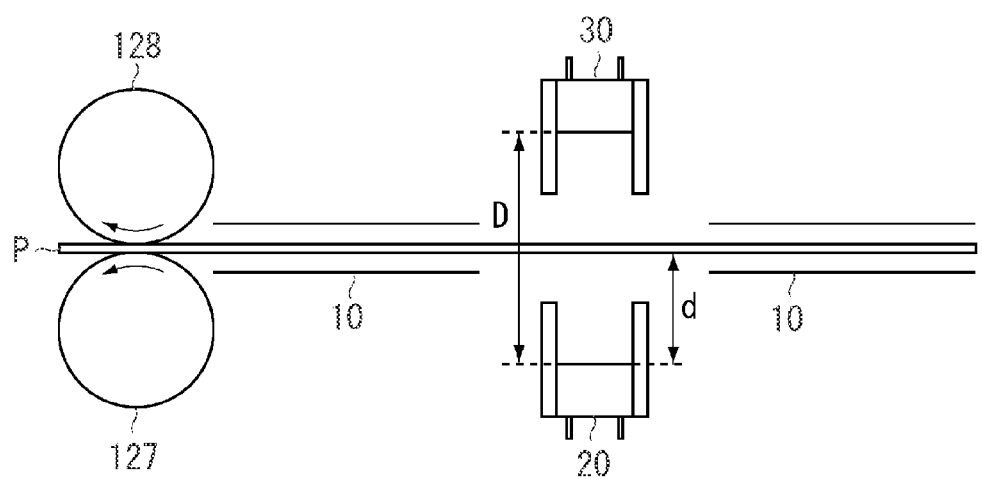
FIG. 3 is a configuration diagram of a grammage sensor according to the exemplary embodiments of the present invention.

FIG. 3 is a schematic view of the recording medium determination apparatus. The ultrasonic transmitter 20 transmits an ultrasonic wave. The ultrasonic receiver 30 receives an ultrasonic wave transmitted from the ultrasonic transmitter 20. The ultrasonic transmitter 20 and the ultrasonic receiver are disposed to face each other. The recording medium P forwarded by the conveyance roller 128 and the opposing conveyance roller 127 on the conveyance path 10 is conveyed between the ultrasonic transmitter 20 and the ultrasonic receiver 30.

The ultrasonic transmitter 20 and the ultrasonic receiver 30 are disposed such that the outgoing surface and the receiving surface are spaced apart by a distance D. The recording medium P is conveyed between the ultrasonic transmitter 20 and the ultrasonic receiver 30, and the ultrasonic transmitter 20 and the ultrasonic receiver 30 are disposed such that the recording medium P is spaced apart from the ultrasonic transmitter 20 and the ultrasonic receiver 30 by a distance d=D/2, respectively. However, in an actual situation, the recording medium P may flutter while being conveyed, and therefore the distance d varies in the range of d≈D/2.

The ultrasonic transmitter 20 and the ultrasonic receiver 30 have a similar configuration, and are respectively constituted by a piezoelelectric element which is an electricity-mechanical energy conversion element, and an electrode terminal. In the ultrasonic transmitter 20, the piezoelelectric element thereof oscillates when pulse voltage is input to the electrode terminal, whereby an ultrasonic wave is transmitted and is propagated in the air. When the ultrasonic wave reaches the recording medium P, the recording medium P oscillates according to the density of the ultrasonic wave. The oscillation of the recording medium P causes also the air at the opposite side to oscillate, so that the ultrasonic wave transmitted from the ultrasonic transmitter 20 is propagated to the ultrasonic receiver 30 via the recording medium P. The piezoelelectric element of the ultrasonic receiver 30 generates output voltage according to the amplitude of the oscillation of the air to the electrode terminal. This is a basis of the method for determining the recording medium P with use of an ultrasonic piezoelelectric element.

A guide member for guiding an ultrasonic wave transmitted from the ultrasonic transmitter 20, and a guide member for guiding an ultrasonic wave which has passed through the recording medium P to the ultrasonic receiver 30 may also be provided. By providing the guide members, it is possible to reduce an influence of a reflection wave of an ultrasonic wave from peripheral members as well as improve the directionality of an ultrasonic wave transmitted from the ultrasonic transmitter 20 to reduce attenuation of the ultrasonic wave received by the ultrasonic transmitter 30.

Figure 4:
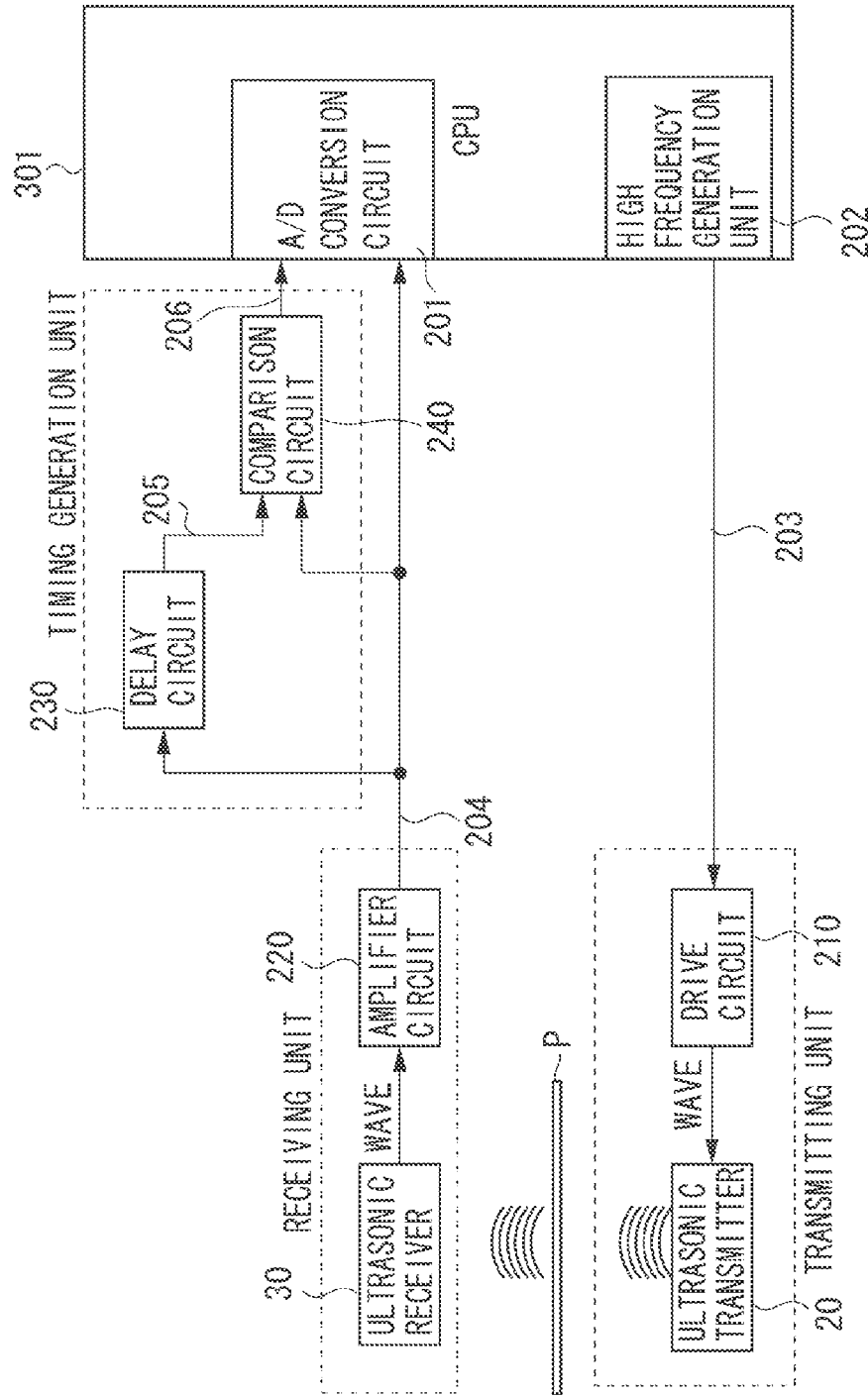
FIG. 4 is a block diagram of a control circuit according to a first exemplary embodiment.

FIG. 4 is a block diagram illustrating a control circuit of the recording medium determination apparatus. The CPU 301 drives a high-frequency generation unit 202 to generate a high-frequency signal 203. The high-frequency generation unit 202 generates the drive signal 203 having a specified frequency, and transmits it to a transmitting unit. The transmitting unit amplifies the received drive signal 203 by a drive circuit 210, and transmits it to the ultrasonic transmitter 20. The ultrasonic transmitter 20 transmits an ultrasonic wave based on the amplified drive signal 203.

In the present exemplary embodiment, the frequency to drive the ultrasonic transmitter 20 is 40 kHz and a wavelength of the ultrasonic wave is approximately 9 mm. This is because the resonance frequency of the piezoelelectric elements of the ultrasonic transmitter 20 and the ultrasonic receiver 30 is 40 kHz. The frequency of 40 kHz is merely an example in the present exemplary embodiment. The frequency of ultrasonic wave is not limited to 40 kHz in a case that the characteristic of the piezoelelectric elements is changed.

The ultrasonic receiver 30 receives an ultrasonic wave transmitted from the ultrasonic transmitter 20 or an ultrasonic wave which has passed through the recording medium P. The received ultrasonic wave is amplified by an amplifier circuit 220, and then is transmitted to a timing generation unit as an intensity signal 204 of the ultrasonic wave. The timing generation unit delays the received intensity signal 204 by a delay circuit 230. A delay signal 205 and the intensity signal 204 are compared with each other by a comparison circuit 240, and then an A/D timing output signal 206 is generated. The A/D timing output signal 206 is transmitted to the CPU 301, which then causes an A/D conversion circuit 201 to operate at the timing of the trailing edge of the A/D timing output signal 206. The CPU 301 determines the recording medium P with use of the result of the A/D conversion at the A/D conversion circuit 201.

Figure 5:
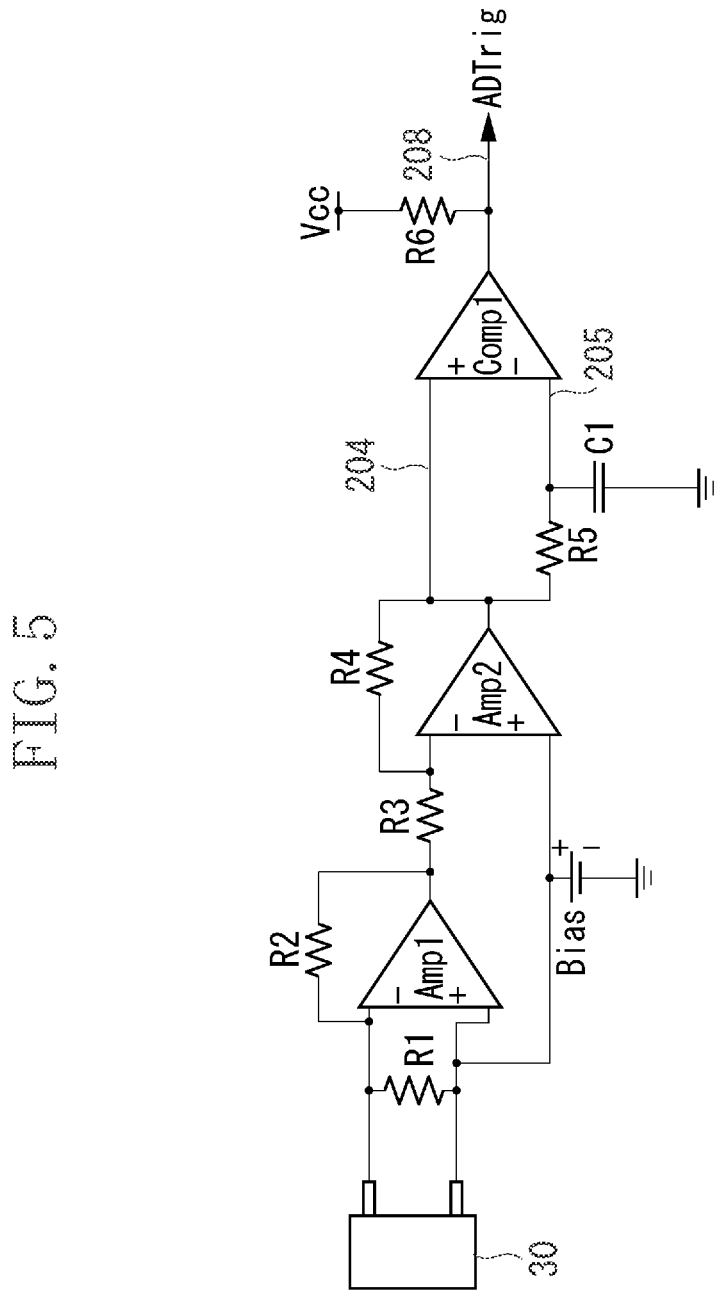
FIG. 5 is a circuit configuration diagram of a timing generation unit according to the first exemplary embodiment.
Figure 6A:
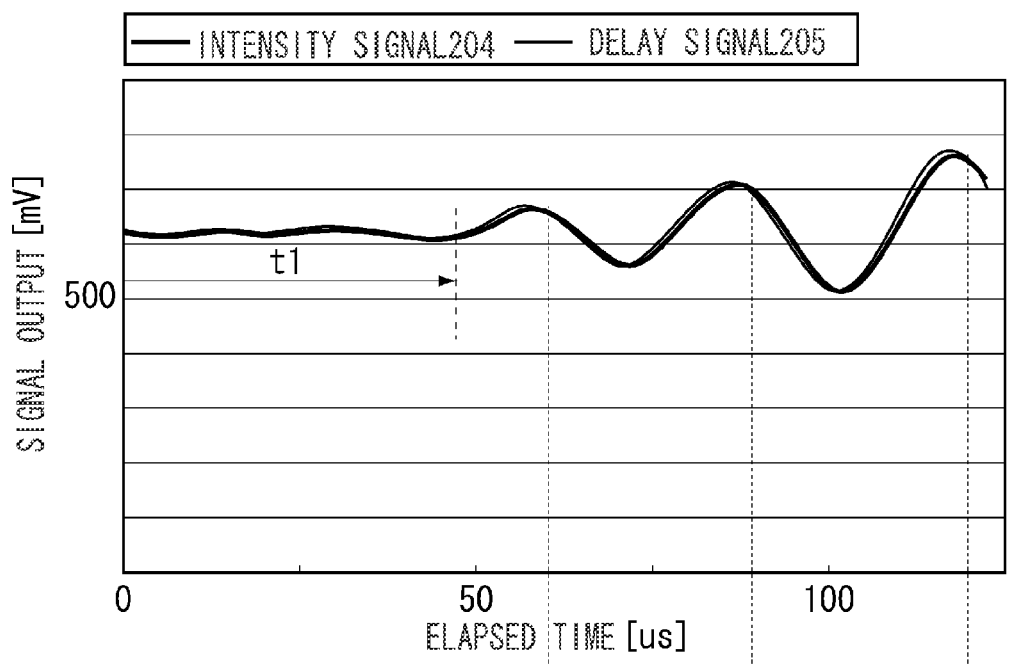
FIGS. 6A and 6B illustrate signal waveforms according to the first exemplary embodiment.
Figure 6B:
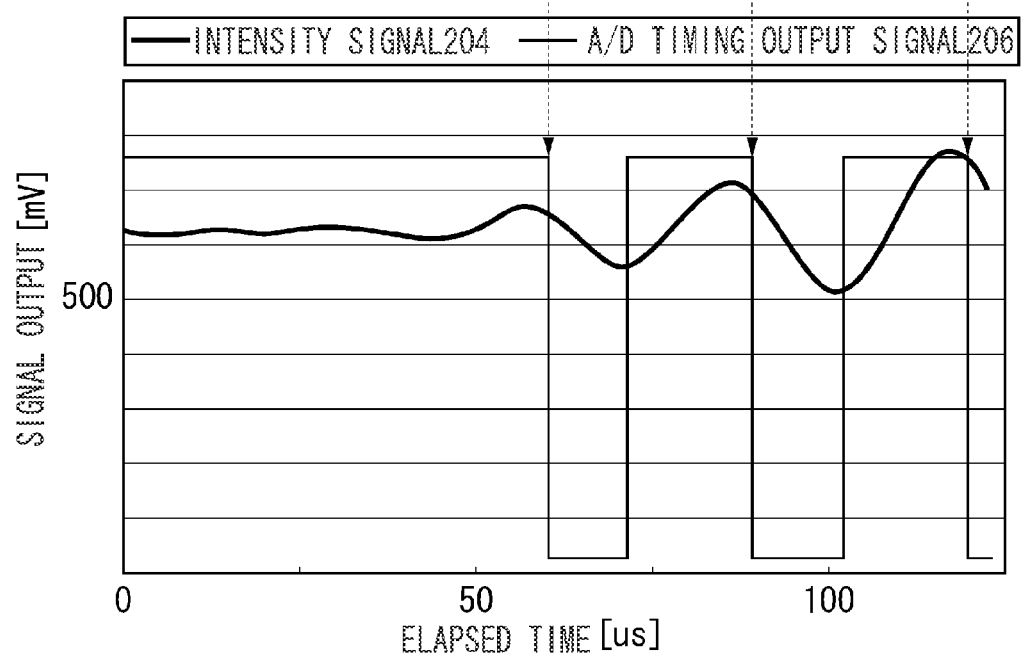

FIG. 5 illustrates an example of a concrete circuit configuration of the timing generation unit. FIG. 6 illustrate a part of signal waveforms in the circuit. A resistance R1 is a load resistance of the ultrasonic receiver 30. The amplifier circuit 220 has a two-stage configuration. First, an output of the ultrasonic receiver 30 is subjected to a conversion from current to voltage at an amplifier circuit constituted by an amplifier circuit Amp1 and a resistance R2, which corresponds to the first stage. Then, the voltage is amplified at an amplifier circuit constituted by an amplifier circuit Amp2 and resistances R3 and R4, which corresponds to the second stage, thereby amplifying the received signal and outputting the intensity signal 204 (204 in FIG. 6A). A delay circuit 230 is constituted by a resistance R5 and a capacitor C1. The delay circuit 230 delays the input intensity signal 204 in advance by the resistance R5 and the capacitor C1 based on a predetermined time constant, and outputs the delay signal 205 (205 in FIG. 6A). A comparison circuit 240 constituted by a comparator Comp1 and a resistance R6 compares the intensity signal 204 and the delay signal 205, and generates the A/D timing output signal 206 (206 in FIG. 6B).

FIG. 6A illustrates the waveform of the intensity signal 204 obtained by amplifying an ultrasonic wave received by the ultrasonic receiver 30. The output gradually increases after a predetermined time t1 has passed since the ultrasonic transmitter 20 transmitted the ultrasonic wave. The predetermined time t1 varies depending on, for example, the distance between the ultrasonic transmitter 20 and the ultrasonic receiver 30, and the ambient environment (temperature and humidity). Generally, a sonic speed is expressed by the following equation:

$$V = \sqrt{\gamma \frac{p}{d}} = 331.5 + 0.607 t \text{(m/s)} \quad (1)$$

in which t represents a temperature [° C.], p represents a pressure, d represents a density, v represents a sonic speed, and γ represents a ratio of constant pressure specific heat and constant volume specific heat of air.

Here, it is assumed that the distance D between the ultrasonic transmitter 20 and the ultrasonic receiver 30 is not changed. Accordingly, a change in the predetermined time t1 can be calculated from a change in the temperature. For example, if the temperature is changed from 20° C. to 30° C., Δt1 is expressed by the following equation:

$$\Delta t1 = \frac{20 \cdot 10^{-3}}{331.5 + 0.607 \cdot 20} - \frac{20 \cdot 10^{-3}}{331.5 + 0.607 \cdot 30} = 1.08 \ [\mu s]. \quad (2)$$

Further, in the equation (1), since p and d are in a proportional relationship, the sonic speed is not changed by a pressure change. In other words, the predetermined time t1 is not affected by an atmospheric pressure change. Further, an experiment has revealed that the predetermined time t1 is changed by 1 to 2 μs according to a paper type of the recording medium P.

For the above-mentioned reason, in the method in which an output value for use in a determination of the recording medium P is obtained after a fixed time has passed, accurate grammage detection cannot be carried out since an ultrasonic wave drive signal was transmitted, since the measurement timing varies depending on a change in the temperature and a change in the recording medium P.

In the present exemplary embodiment, first, the A/D timing output signal 206, which is a square wave, is obtained from the intersection points of the intensity signal 204 and the delay signal 205 as a trigger for obtaining an output value for use in a determination of the recording medium P. The A/D conversion circuit 201 mounted in the CPU 301 starts an A/D conversion at the timing of the trailing edge of the obtained A/D timing output signal 206, obtains a voltage value of the intensity signal 204, and provides an output value for use in a determination of the recording medium P. In this way, instead of obtaining an output value for use in a determination of the recording medium P after a fixed time has passed since an ultrasonic wave was transmitted, an output value is obtained at the timing of the trailing edge of the A/D timing output signal 206 derived from the intersection points of the intensity signal 204 and the delay signal 205. Therefore, it is possible to obtain an output value at the timing suitable for each environmental condition and each type of the recording medium P according to an environmental condition and a type of the recording medium P, so that the accuracy of a determination of the recording medium P can be improved. In the present exemplary embodiment, the trailing edge of the A/D timing output signal 206 is employed as the timing of obtaining an output value for use in a determination of the recording medium P. However, the leading edge thereof may be employed instead. Further, timing of a reversed output may be obtained by exchanging a plus-side input terminal and a minus-side input terminal of the comparator Comp1. Further, both positive and negative local maximum values may be used, or a plurality of local maximum values may be used.

Further, in the present exemplary embodiment, the output value in the third cycle of A/D conversion result is employed as a value for use in a determination of the recording medium P. This is because the output value in the third cycle is suitable for a determination of the recording medium P, as will be described in detail below. Employing the output value in the third cycle is merely an example, and the timing is not limited to the third cycle as long as it is possible to ensure the accuracy of a determination of the recording medium P.

Figure 7:
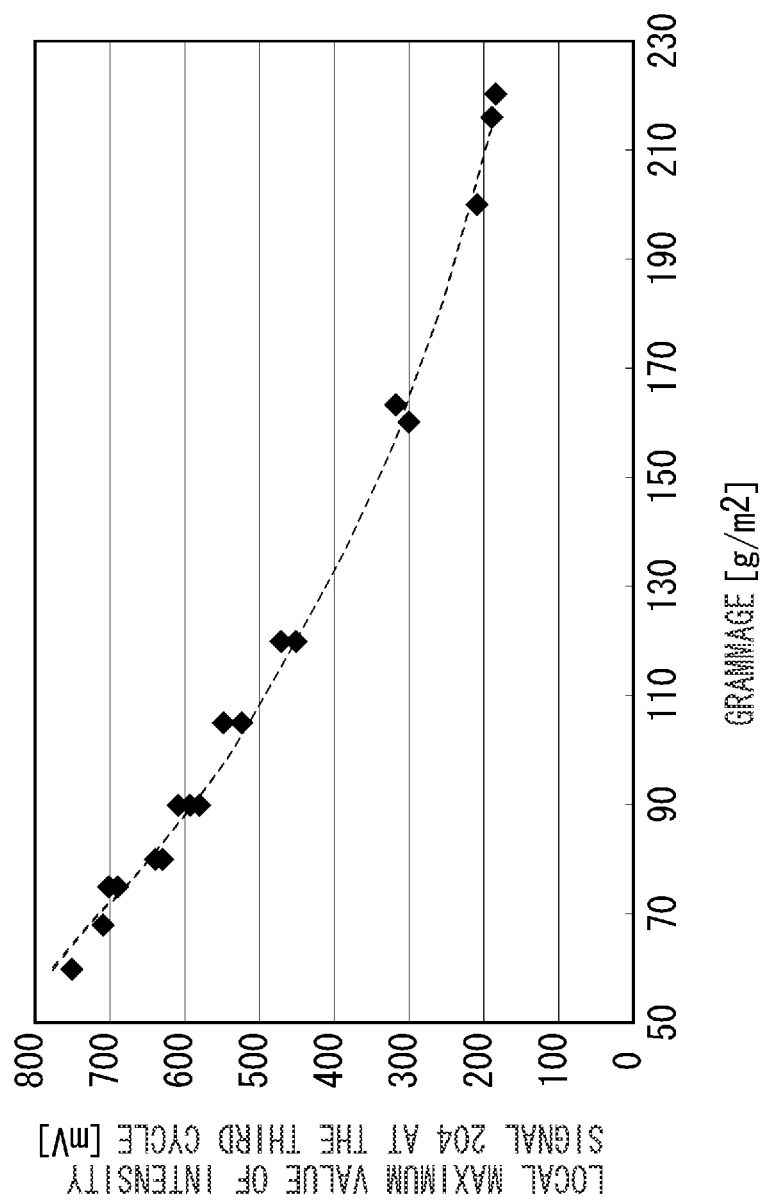
FIG. 7 illustrates the relationship between the local maximum value of an intensity signal and the grammage according to the first exemplary embodiment.

FIG. 7 illustrates the relationship between the local maximum value of the intensity signal 204 in the third cycle and the grammage. This figure illustrates the relationship between the grammage in the range of 60 [g/cm$^2$] to 220 [g/cm$^2$] and the local maximum value as an example. Here, a graph which can nearly uniquely determine a local maximum value for each grammage is obtained by using the local maximum value of the intensity signal 204 in the third cycle for a determination of the recording medium P. For example, a local maximum value corresponding to the recording medium P having a grammage of 110 [g/cm$^2$] is approximately 500 [mV]. Since it is possible to derive such a relationship between the local maximum value and the grammage, a determination of the recording medium P can be accurately carried out. The timing of obtaining the local maximum value of the intensity signal 204 is not limited to the third cycle, as long as it is possible to obtain such an output value as the relationship between the local maximum value and the grammage can be uniquely determined likewise.

Figure 8:
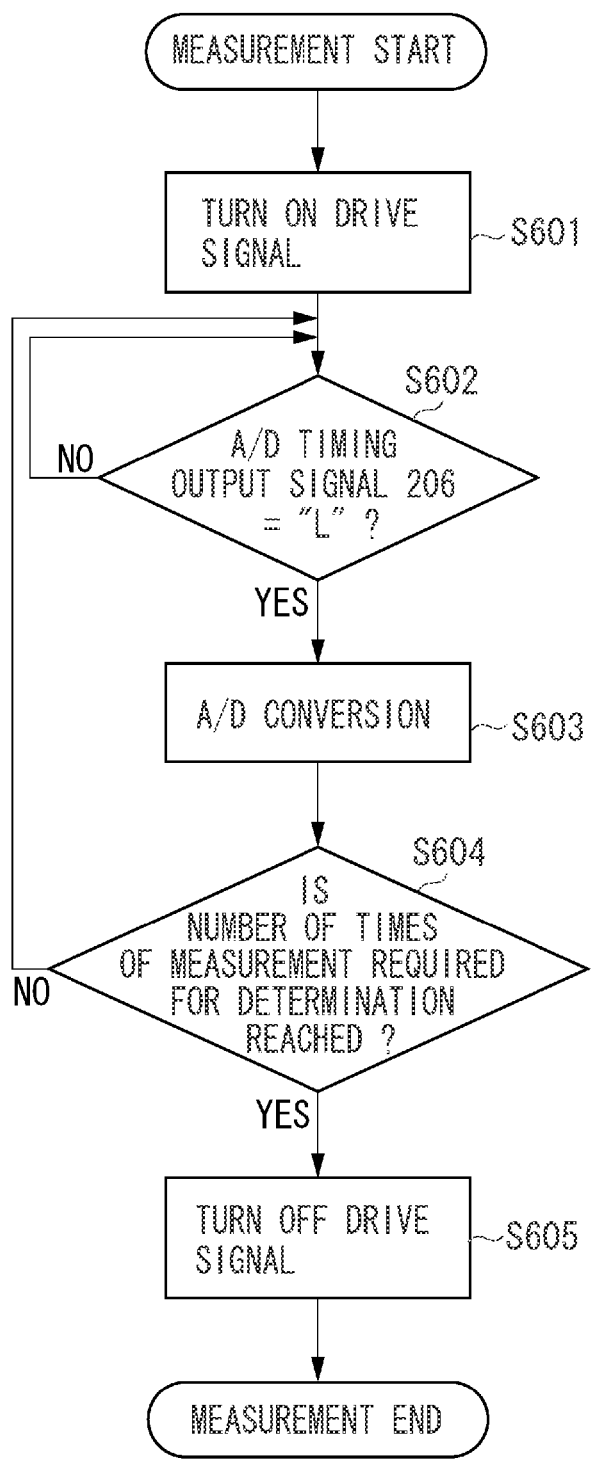
FIG. 8 is a flowchart illustrating an operation of a CPU according to the first exemplary embodiment.

FIG. 8 is a flowchart illustrating an operation of the CPU 301. In step S601, the CPU 301 turns on a drive signal for driving an ultrasonic wave to start determining the recording medium P. Then, in step S602, the CPU 301 monitors the trailing edge of the A/D timing output signal 206 derived from the intensity signal 204 and the delay signal 205 of the received ultrasonic wave after the ultrasonic wave is transmitted and the ultrasonic wave which has passed through the recording medium P is received. In step S603, the CPU 301 causes an A/D conversion of the intensity signal 204 in synchronization with the trailing edge of the A/D timing output signal 206. The CPU 301 repeats the monitoring of the A/D timing output signal (step S602) and the A/D conversion (step S603) until the number of times of measurement required for a determination of the recording medium P is reached (step S604). If the required number of times of measurement is reached, in step S605, the CPU 301 turns off the drive signal.

In this way, the timing of obtaining an output value for use in a determination of the recording medium P is generated from a received signal of an ultrasonic wave and a delay signal generated by delaying the received signal of the ultrasonic wave for a predetermined time, whereby it is possible to reduce an influence of reflection from the peripheral members and an influence of a change in the environment to improve the accuracy of grammage detection.

A second exemplary embodiment of the present invention performs a control by using a peak hold of a received signal as the comparison signal generation method of the timing generation unit described in the first exemplary embodiment. In the following description of the second exemplary embodiment, the same configuration as the configuration of the above-mentioned first exemplary embodiment will not be described.

Figure 9:
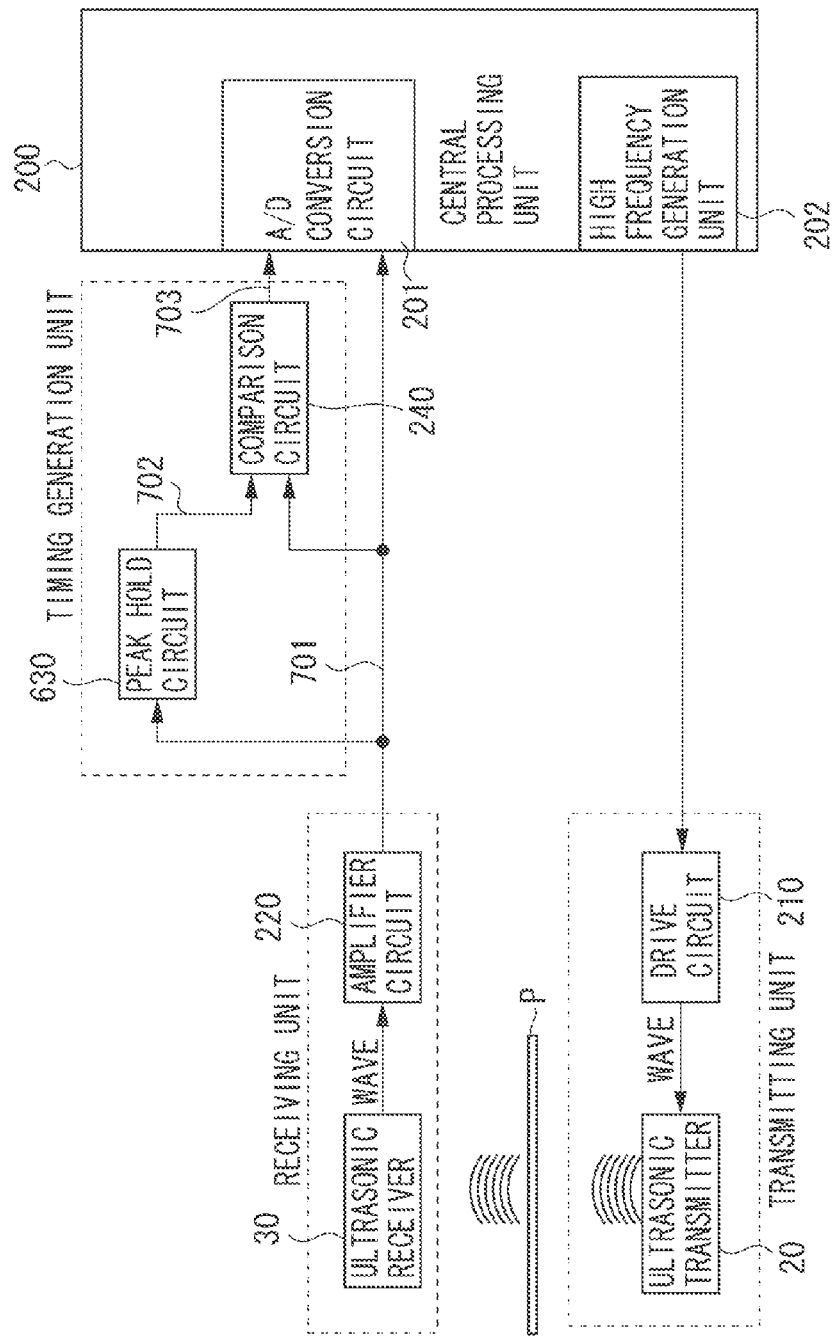
FIG. 9 is a block diagram of a control circuit according to a second exemplary embodiment.
Figure 10:
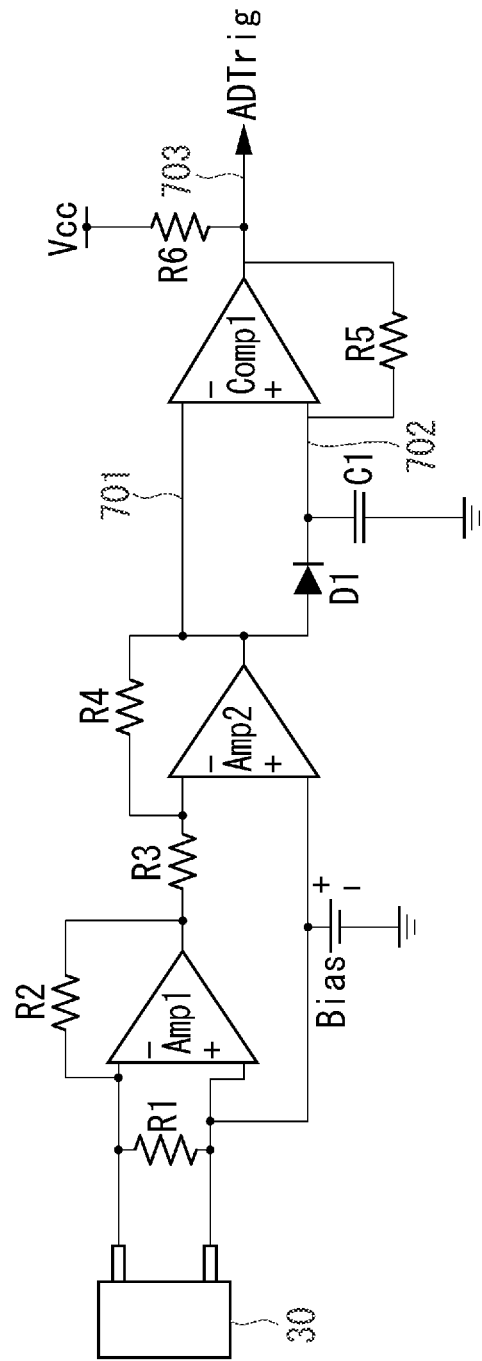
FIG. 10 is a circuit configuration diagram of a timing generation unit according to the second exemplary embodiment.

FIG. 9 is a block diagram illustrating a control circuit of the recording medium determination apparatus. FIG. 10 illustrates an example of a concrete circuit configuration of a receiving unit and a timing generation unit in the control circuit. A difference between the control circuit shown in FIG. 9 and the control circuit in the before-described first exemplary embodiment is that the control circuit shown in FIG. 9 employs a peak hold circuit 630 as a waveform generator at the timing generation unit. As shown in the concrete circuit configuration of FIG. 10, the peak hold circuit 630 is constructed using a diode D1 and a capacitor C1.

Figure 11A:
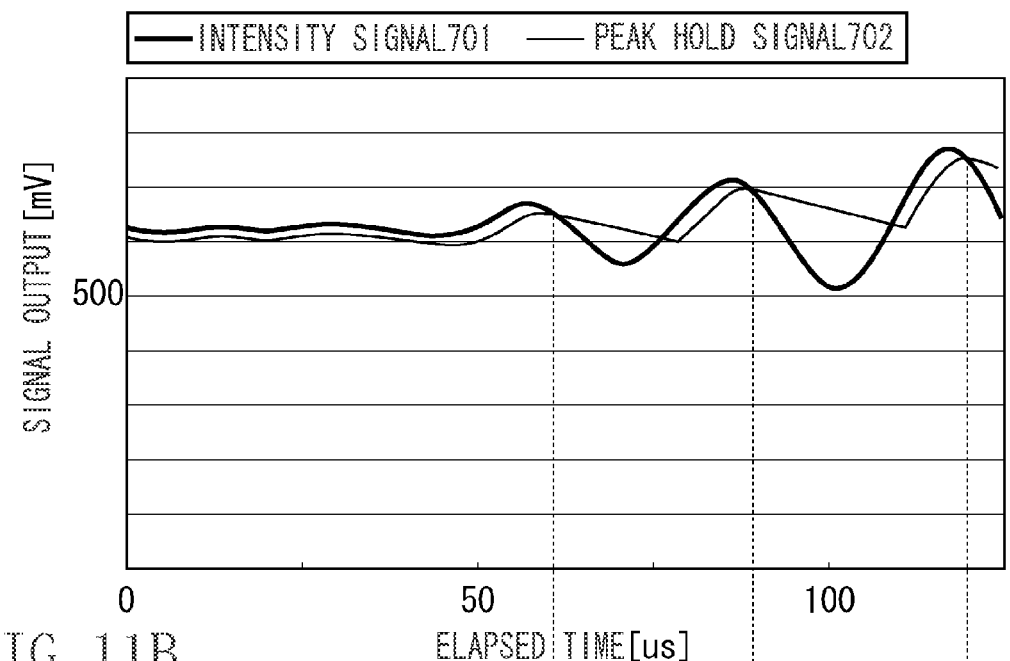
FIGS. 11A and 11B illustrate signal waveforms according to the second exemplary embodiment.
Figure 11B:
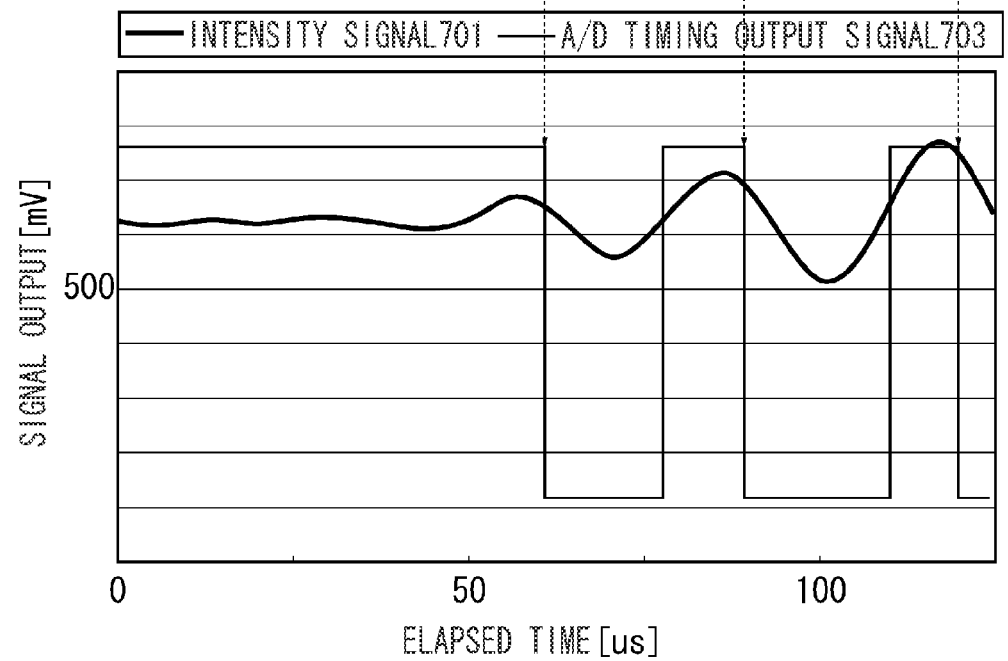

FIG. 11 illustrate a part of the signal waveforms in the circuit shown in FIG. 10. The received signal received by the ultrasonic receiver 30 is amplified by the amplifier circuit 220 and is output as an intensity signal 701. If the voltage of the intensity signal 701 exceeds the voltage obtained by adding the amount of charge accumulated in the capacitor C1 and the forward voltage Vf of the diode D1, the capacitor C1 is charged. If the voltage of the intensity signal 701 does not exceed the voltage obtained by adding the amount of charge accumulated in the capacitor C1 and the forward voltage Vf of the diode D1, the capacitor C1 is not charged. Therefore, as shown in FIG. 11A, a peak hold signal 702 holds the peak voltage of the intensity signal 701. Here, the discharge curve of the peak hold signal 702 is determined based on a time constant T of the capacitor C1 and a resistance R5. In order to operate the peak hold circuit 630 normally, the time constant T should be sufficiently increased by a time constant circuit compared to the frequency of ultrasonic wave set at the transmitting unit.

An A/D timing output signal 703 (703 in FIG. 9B) is generated by comparison of the intensity signal 701 and the peak hold signal 702 at the comparison circuit 240. The trailing edge of the generated A/D timing output signal 703 is used as the timing of obtaining an output value for use in a determination of the recording medium P.

In this way, the A/D timing output signal 703, which is generated by the delay circuit 230 in the first exemplary embodiment, can be generated by the peak hold circuit 630 in the second exemplary embodiment. It is possible to reduce an influence of reflection from the peripheral members and an influence of a change in the environment to improve the accuracy of grammage detection, by using the A/D timing output signal 703 generated with use of the peak hold circuit 630. It should be noted that, although the A/D timing output signal 703 is generated by the delay circuit 230 or the peak hold circuit 630 in the above-mentioned exemplary embodiments, any circuit is useful which enables generation of the A/D timing output signal 703 for use in a determination of the recording medium P, and is not limited to the delay circuit 230 and the peak hold circuit 630.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-285756 filed Dec. 16, 2009 and No. 2010-235489 filed Oct. 20, 2010, which are hereby incorporated by reference herein in their entirety.

What is claimed is:

1. A recording medium determination apparatus comprising:
   a transmitting unit configured to transmit an ultrasonic wave to a recording medium;
   a receiving unit configured to receive the ultrasonic wave via the recording medium;
   a delay unit configured to delay the received ultrasonic wave for a predetermined time;
   a generation unit configured to generate a timing of detecting an output value of the received ultrasonic wave from the received ultrasonic wave and the delayed ultrasonic wave; and
   a control unit configured to determine the recording medium using the output value of the received ultrasonic wave at the timing generated by the generation unit.

2. The recording medium determination apparatus according to claim 1, wherein the generation unit generates a square wave from an intersection point of the received ultrasonic wave and the delayed ultrasonic wave.

3. The recording medium determination apparatus according to claim 2, wherein the control unit determines the recording medium using the output value of the received ultrasonic wave at the timing of the trailing edge of the square wave.

4. The recording medium determination apparatus according to claim 2, wherein the control unit determines the recording medium using the output value of the received ultrasonic wave at the timing of the leading edge of the square wave.

5. The recording medium determination apparatus according to claim 1, wherein the control unit determines the grammage of the recording medium.

6. An image forming apparatus comprising:
   an image forming unit configured to form an image;
   a transmitting unit configured to transmit an ultrasonic wave to a recording medium;
   a receiving unit configured to receive the ultrasonic wave via the recording medium;
   a delay unit configured to delay the received ultrasonic wave for a predetermined time;
   a generation unit configured to generate a timing of obtaining a value for use in a determination of the recording medium based on the received ultrasonic wave and the delayed ultrasonic wave; and
   a control unit configured to control the image forming unit using the output value of the received ultrasonic wave at the timing generated by the generation unit.

* * * * *